United States Patent

Mölter et al.

[11] Patent Number: 5,815,265
[45] Date of Patent: Sep. 29, 1998

[54] DEVICE AND METHOD FOR MEASURING A PARTICLE FLOW IN A FLUID

[75] Inventors: Leander Mölter, Wörth; Friedrich Munzinger, Gondelsheim, both of Germany

[73] Assignee: Palas GmbH Partikel-und LasermeBtechnik, Kalsruhe, Germany

[21] Appl. No.: 890,999

[22] Filed: Jul. 10, 1997

[30] Foreign Application Priority Data

Jul. 12, 1996 [DE] Germany .................. 196 28 156.3

[51] Int. Cl.$^6$ ............................ G01N 21/00; G02B 26/02
[52] U.S. Cl. ............ 356/338; 356/339; 356/442; 250/574; 359/232; 359/233
[58] Field of Search ................. 356/335–343, 356/441–442; 250/564, 573, 574; 359/227, 232–233

Primary Examiner—Frank G. Font
Assistant Examiner—Jason D. Vierra-Eisenberg
Attorney, Agent, or Firm—Antonelli, Terry, Stout & Kraus, LLP

[57] ABSTRACT

For simplifying the optical measurement of a particle flow in a fluid and in particular for eliminating errors, in a device for measuring a particle flow in a fluid with at least one illumination system having a diaphragm and at least one receiver system having a diaphragm, the invention provides for a diaphragm (6a, 11a) to have an aperture (6, 11) with an edge (6b, 11b) constructed convexly towards the interior of the diaphragm aperture (6, 11). According to a method, the particle flow is illuminated and/or observed through a diaphragm aperture with an edge constructed convexly towards its interior and the maximum intensity of the particle flying through a first optical measuring range is measured and account is only taken of the particle if the intensity on flowing through a second measuring range exceeds a specific minimum percentage of the maximum intensity measured for this particle.

15 Claims, 3 Drawing Sheets

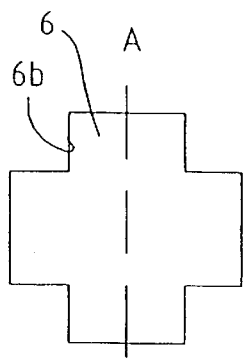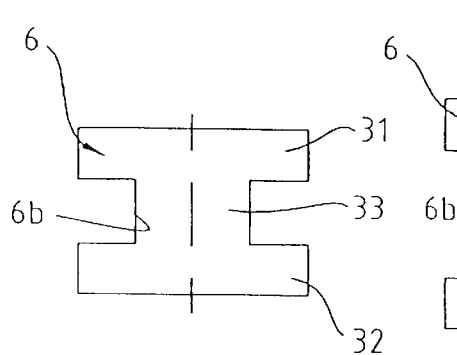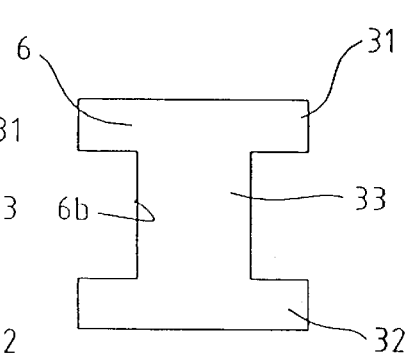
Fig 5a  Fig 5b  Fig 5c
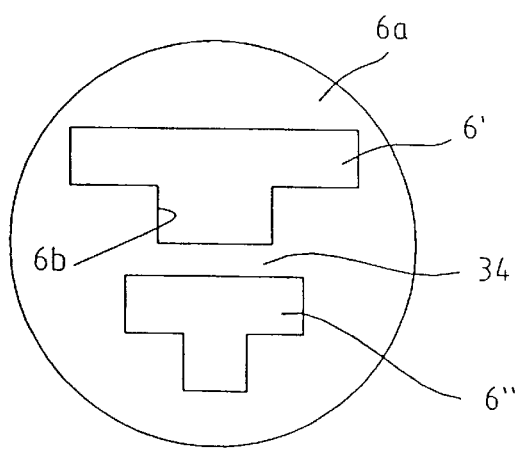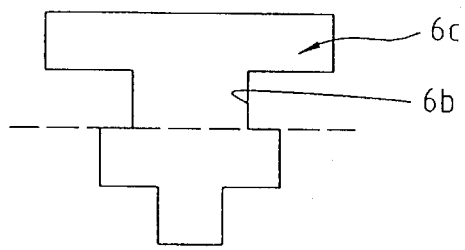
Fig 6  Fig 7a
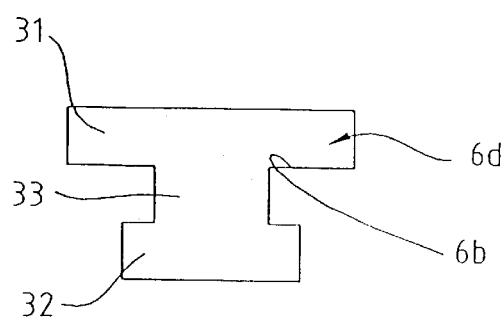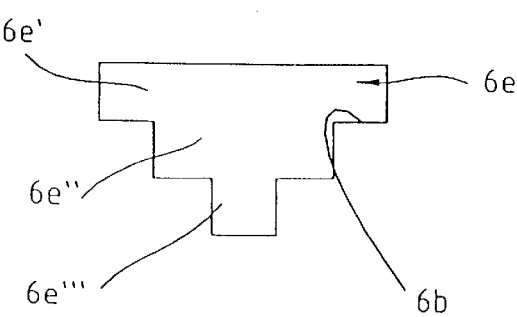
Fig 7b  Fig 7c

DEVICE AND METHOD FOR MEASURING A PARTICLE FLOW IN A FLUID

FIELD OF THE INVENTION

The invention relates to a device for measuring a particle flow in a fluid with at least one illumination system having a diaphragm and with at least one receiver system having a diaphragm and a method for measuring a particle flow in a fluid, the particle flow being illuminated and light scattered by particles is detected under a finite angle to the illumination direction.

BACKGROUND OF THE INVENTION

A particle flow to be measured in a fluid can be in the form of a solid or liquid particles in a gas or in a liquid. Such measurements are performed in order generally to determine the particle size distribution and particle concentration in the fluid. The particle size is proportional to the light intensity scattered by a particle on a receiver and the concentration is determined via counting pulses. In particular for the determination of a particle size errors can occur if particles, which are partially located in the optical measuring volume and are partially located outside the same, therefore scatter only a lower light intensity onto the receiver than corresponds to their size. Such errors can be excluded. This has hitherto been brought about in that the scattered light was determined by two detector systems by means of coincidence measurements, the detector systems having diaphragm apertures of different size. This requires high apparatus costs. In addition, such a measurement can lead to errors, if the particles do not have a uniform scattering action.

The problem of the invention is therefore to provide a device and a method with which, whilst avoiding the aforementioned errors, accurate measurements can be achieved with lower apparatus costs.

SUMMARY OF THE INVENTION

In the case of a device of the aforementioned type, the set problem is inventively solved in that at least one diaphragm has a diaphragm aperture with an edge constructed convexly towards the interior of the diaphragm aperture. For the solution of the set problem, a method according to the invention provides for the particle flow is illuminated and/or observed through a diaphragm aperture with an edge constructed convexly towards its interior, that the maximum intensity of the particle flying through a first optical measuring range is measured and the particle is only taken into account if the intensity on flying through a second measuring range exceeds a specific minimum percentage of the maximum intensity measured for this particle.

As a result of the diaphragm aperture provided with an edge direct convexly towards the interior, said diaphragm is subdivided into two or more areas, through which on imaging the diaphragm in the particle flow different measuring ranges are defined. A particle flying through close to the edge of the wider diaphragm area or wider measuring range will remain outside the narrower diaphragm area or the resulting measuring range and will consequently no longer be detected in the latter. The scattered light pulse of such a particle will have a shorter time period than a particle flying centrally through the diaphragm. The first-mentioned particle can consequently be excluded during the measurement, which takes place in the manner characterized by said method.

Thus, with a receiver system (and an illumination system) edge errors can be excluded and consequently the apparatus costs for the fault-free measurement of a particle flow in a fluid are reduced.

According to a preferred development, the edge has a steplike construction, the diaphragm aperture being T-shaped or H-shaped. In the first mentioned case, according to further developments, the length of the T-leg is the same as the thickness of the T-crossbar and the T-leg is oriented in the particle flow direction. In the second-mentioned case, the length of the H-crossbar connecting the H-legs is the same as the thickness of the H-longitudinal leg or the length of the H-crossbar connecting the H-legs is twice the thickness of the H-longitudinal leg in each case the H-crossbar is oriented in the particle flow direction.

According to further preferred developments of the device according to the invention, both the diaphragm aperture of the imaging system and the diaphragm aperture of the receiver system is constructed with convex edges and that a diaphragm with two diaphragm apertures has different dimensions. The diaphragm apertures are to be sharp-edged and burr-free.

According to a further development of the method according to the invention, as the second measured value the particle intensity is determined following a time representing roughly the average through-flow time of the particle through the first optical measuring range after establishing the maximum intensity and only those particles are detected which on flowing through the second optical measuring range give a relative signal intensity of at least 20% of the measured maximum intensity.

BRIEF DESCRIPTION OF THE DRAWINGS

Further advantages and features of the invention can be gathered from the claims and following description describing embodiments with reference to the attached drawings, wherein show:

FIGS. 5*a*–5*c* Other configurations of diaphragm apertures according to the invention.

FIG. 6 A design of a double diaphragm according to the invention.

FIGS. 7*a*–7*c* Further configurations of diaphragm apertures according to the invention.

DETAILED DESCRIPTION OF THE DRAWINGS

Figure 1:
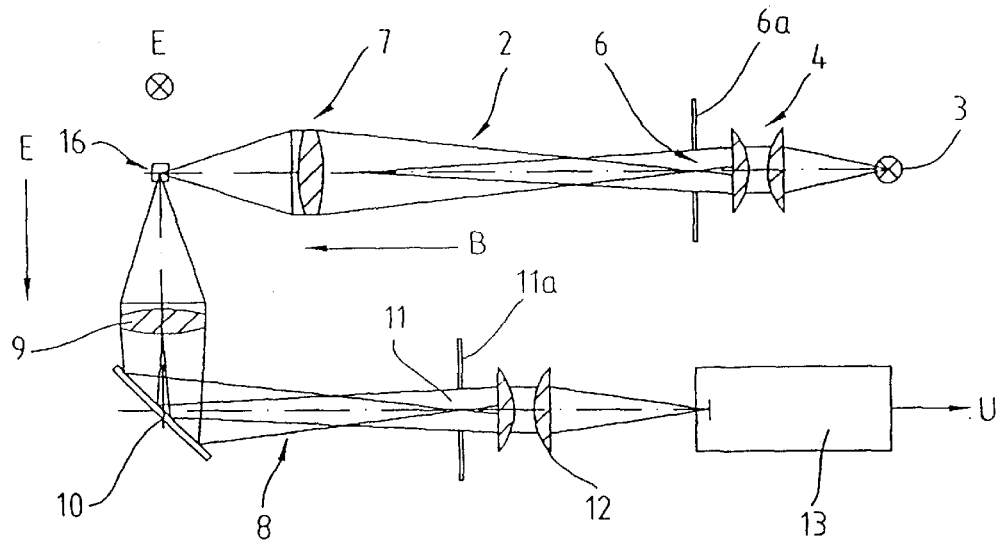
FIG. 1 A diagrammatic representation of a device according to the invention.

For the measurement of a particle flow in a fluid, such as for measuring an aerosol, there is an illumination of the particle flow by an illumination system 2 with a light source 3, which is preferably a white light source, a condenser system 4, a diaphragm aperture 6 in a diaphragm 6*a* and an imaging optics 7. The particle flow is observed by means of a receiver system 8 with an imaging optics 9, a further diaphragm aperture 11 in a further diaphragm 11*a,* a further condenser system 12 and an optoelectrical receiver 13. In the represented embodiment there is also a reflecting mirror 10, which is not necessary, for the parallel arrangement of light source and receiver. The signal supplied by the receiver 13 is processed in a following electronic means.

The imaging optics 9 of the receiver system 8 is such that it images the diaphragm aperture 11 where the imaging optics 7 images the diaphragm aperture 6 in the particle flow. Thus, optically a measuring volume 16 is formed in the crossing area of the illumination beam 17 and the receiver beam 18 within the particle flow.

The particle flow generally flows perpendicular through the plane formed by the illuminating the receiver beams 17, 18, i.e. perpendicular to the plane of the page in FIG. 1.

However, according to the invention, the diaphragm apertures 6, 11 are constructed with convex edges directed towards the interior of the diaphragm aperture. In all the represented embodiments the convexity is achieved by steps or shoulders on the boundary of the diaphragm aperture. In the represented embodiment the diaphragm apertures 6, 11 in each case form a T, as can be gathered from FIG. 2, where for illustration purposes the diaphragm apertures 6, 11 are projected into the beam plane 17, 18. The illumination direction is here, as in FIG. 3, defined by B, the receiving light beam direction by E and the particle flow by A. The T-shaped diaphragm apertures, 6, 11 have a T-longitudinal leg 21 and a T-crossbar 22. The length l of the T-longitudinal leg coincides in the represented embodiment with the thickness s of the T-crossbar 22. The absolute overall dimensions of the diaphragm apertures 6, 11 are consequently defined by the imaging system, the desired measuring volume and the precision of the machining possibilities for the diaphragm and diaphragm apertures, because the latter are to be sharp-edged, with sharp corners and also burr-free. The linear overall dimensions are e.g. approximately 0.5 mm. In the specific embodiment the length of the T-longitudinal leg l=0.250 mm, the thickness of the T-crossbar s=0.250 mm, the total height of the diaphragm apertures 6, 11 H=0.5 mm, the width of the T-longitudinal leg b=0.500 mm and the length of the T-crossbar L=0.650 mm. The diaphragm material thickness is approximately 50 $\mu$m.

Figure 2:
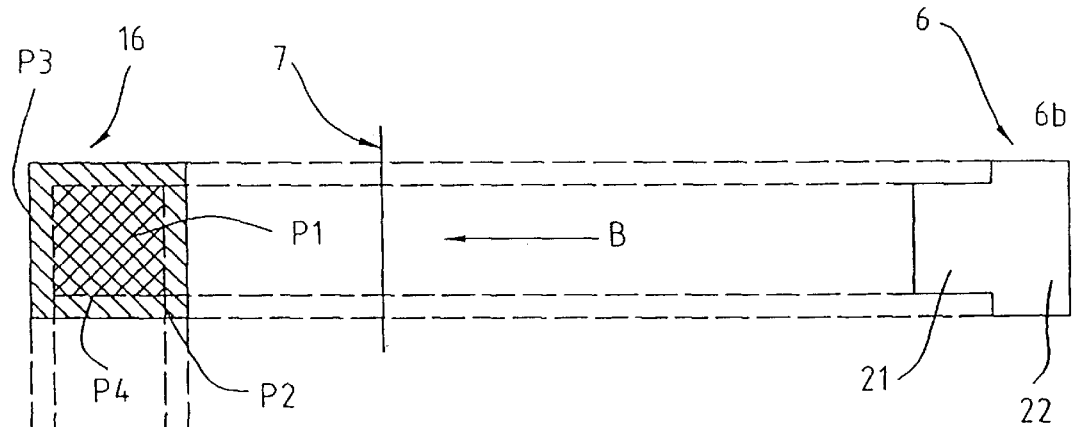
FIG. 2 Diaphragms used according to the invention and the measuring volume optically formed by them in projection.
Figure 3:
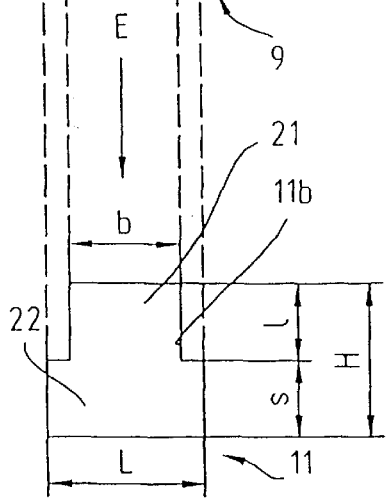
FIG. 3 The measuring volume formed according to the invention in a perspective view.

As a result of the two T-shaped diaphragm apertures 6, 11 shown in FIG. 2, the measuring volume 16 shown in FIG. 3 is optically formed, being shaped like a square mushroom and having two successive measuring ranges 16a, 16b in the flow direction A of the particle flow 1, which have different cross-sectional surfaces perpendicular to the flow direction A of the particle flow 1 (i.e. with surface normals parallel to A). However, in the represented embodiment they have identical heights h in the flow direction corresponding to the coinciding values l and s of the diaphragm apertures 6, 11.

Figure 4:
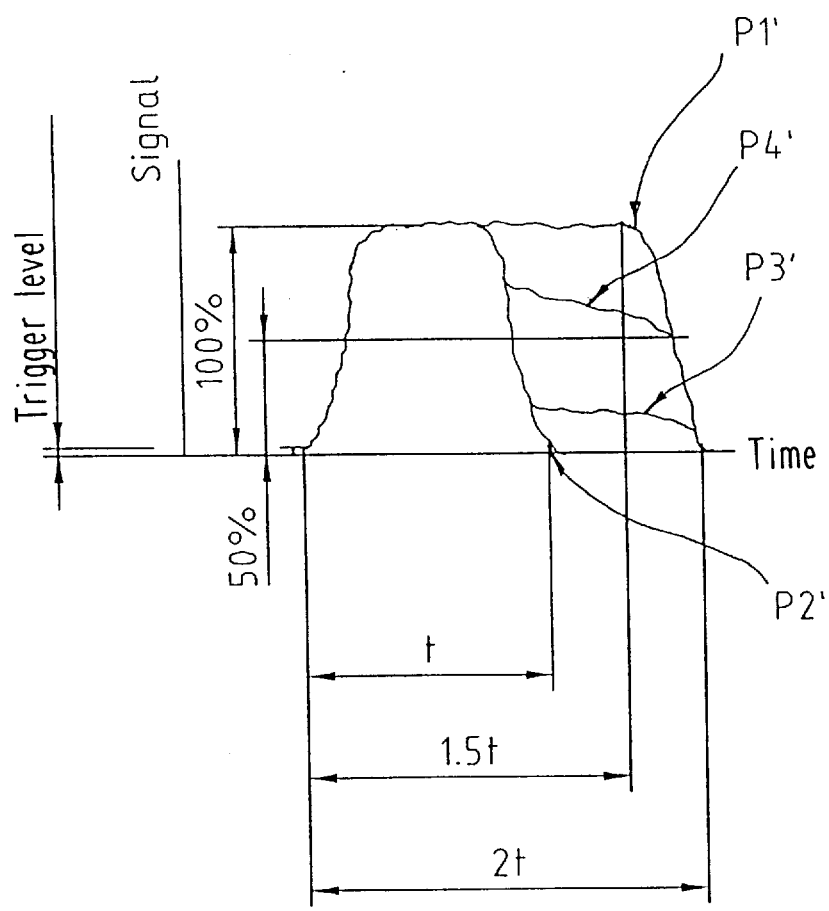
FIG. 4 Signal paths of particles detected by the device according to the invention.

If the particle P1 now flies on a path, so that it passes through both measuring ranges 16a, 16b (FIG. 2), then it scatters light intensity dependent on its size both during time t during which it flies through the measuring range 16a and during the time when it flies through the measuring range 16b and consequently delivers in the receiver 13 the signal P1 in FIG. 4, which is roughly of identical magnitude over the entire through-flight time 2t of the particle P1 through the entire measuring volume 16.

A particle P2, which passes through a marginal portion of the measuring range 16a, only supplies a signal corresponding to its magnitude during the time t when it is in the measuring range 16a, whereas after passing out of the measuring range 16a it does not fly through the smaller measuring range 16b and instead flies past it and consequently no light falls on this particle in the flight height of the measuring range 16b. Therefore no light can be scattered in the receiver 13, so that it only delivers a scattered light signal P2' (FIG. 4) during time t.

A particle P3, which only touches the measuring range 16b with a small area of its volume on its path through the measuring volume 16 or enters said area when the centre of gravity of the particle P3 is outside the measuring range 16b, is consequently only illuminated on its small surface portion projecting into the measuring range 16b and only with said small portion scatters light in the receiver 13, so that the latter only receives the full signal corresponding to the particle size on passing through the first measuring range 16a for the time t, but subsequently has a much smaller signal, as represented overall by P3' in FIG. 4. Compared with the maximum signal determined by the particle size during the transit time t (corresponding to measuring range 16a), the signal intensity on flying through the measuring range 16b is only approximately 20%, as can be gathered from FIG. 4.

A particle P4, which with its largest part flies both through the measuring range 16a and measuring range 16b, but on the edge of the latter in such a way that a smaller surface part of the particle is located outside the measuring range 16b will lead, on flying through range 16b, to a relatively large signal compared with the maximum signal determined by its size. A signal of such a particle is designated P4' in FIG. 4.

In order to avoid any falsification of the measured results, particularly the particle size distribution due to particles where part of their surface is outside the measuring volume, only the particles with their maximum intensity (100%) received during the time t (flight through the measuring range 16a) are counted, which on flying through the measuring range 16b have a signal intensity above the predetermined threshold, which in the represented embodiment of FIG. 4 is 50% of the maximum light intensity are detected, whereas particles which during the flow-through the measuring range 16b have a lower relative signal intensity are discarded for the measurement. In the represented embodiment for measurement purposes use is only made of particles P1 and P4, whereas particles P2 and P3 are discarded.

The minimum threshold S is dependent on the particle size relative to the measuring volume. In the represented embodiment the threshold S could also be lower than 50% of the maximum intensity. The particles can have cross-sectional dimensions which, diverging from FIG. 2, are of the order of magnitude of the measuring volume dimensions and e.g. only represent ⅕ to ⅒ of the measuring volume dimensions. In this case it must be ensured that there is no counting of those particles whereof only a small portion projects over the edge of the measuring range 16a.

Further preferred developments of the inventive diaphragms are shown in FIGS. 5 to 7. FIG. 5a shows a cruciform diaphragm aperture. FIG. 5b shows a H-shaped diaphragm aperture, the H-crossbar 33 connecting the H-legs 31, 32 being oriented in the extension direction A of the particle flow. The thickness S' of the H-legs 31, 32 corresponds to the length l' of the H-crossbar 33. FIG. 5c also shows a H-shaped diaphragm aperture, but here the length l' of the crossbar 33 corresponds to twice the thickness S' of the H-legs 31, 32.

FIG. 6 shows in a diaphragm 6a two T-shaped diaphragm apertures 6', 6" superimposed in the flow direction A. Thus, with the same imaging optics (with which the two diaphragm apertures 6', 6" are imaged in the particle flow for forming the measuring volume), measuring volumes of different size are formed, so that it is possible to increase the dynamic range, i.e. the concentration range, which can be measured with a corresponding device according to the invention.

The material web 34 between the two diaphragm apertures 6', 6" can also be omitted leading to the formation of a diaphragm aperture 6c according to FIG. 7a, different areas being used on the one hand for eliminating undesired particles from the count and on the other for increasing the dynamic range. The diaphragm aperture of FIG. 7a can also follow FIG. 7b, so that the aperture 6d forms a H with legs 31, 32 of different lengths. Optionally, the diaphragm aperture 6c can be simplified to give the diaphragm aperture 6e shown in FIG. 7c. In this case, with no particle concentrations for measuring the diaphragm aperture areas 6e' and 6e" in the case of high particle concentrations the diaphragm aperture areas 6e" and 6e''' are used for deciding whether a particle is to be counted or eliminated.

We claim:

1. Device for measuring a particle flow in a fluid with at least one illumination system having a diaphragm and with at least one receiver system having a diaphragm, characterized in that at least one diaphragm (6a, 11a) has a diaphragm aperture (6, 11) with and edge (6b, 11b) constructed convexly towards the interior of the diaphragm aperture.

2. Device according to claim 1, characterized in that the edge (6b, 6c) is steplike.

3. Device according to claim 1, characterized in that the diaphragm aperture (6, 11) is T-shaped.

4. Device according to claim 3, characterized in that the length (1) of the T-leg (21) is equal to the thickness of the T-crossbar (22).

5. Device according to claim 3, characterized in that the T-leg (21) is directed in the flow direction (A) of the particle flow.

6. Device according to claim 1, characterized in that the diaphragm aperture (6, 11) is H-shaped.

7. Device according to claim 6, characterized in that the length of the H-crossbar linking the H-legs is the same as the thickness of the H-longitudinal leg.

8. Device according to claim 6, characterized in that the length of the H-crossbar connecting the H-legs is twice the thickness of the H-longitudinal leg.

9. Device according to claim 1, characterized in that both the diaphragm aperture of the imaging system (2) and the diaphragm aperture (11) of the receiver system (8) is constructed with convex edges (6b, 11b).

10. Device according to claim 1, characterized in that a diaphragm (6) has two diaphragm apertures (6', 6"), with different dimensions.

11. Device according to claim 1, characterized in that the edges (6b, 11b) of the diaphragm apertures are sharp.

12. Device according to claim 1, characterized in that the edges (6b, 11b) of the diaphragm apertures (6, 11) are free from burrs.

13. Method for measuring a particle flow in a fluid, the particle flow being illuminated and under a finite angle to the illumination direction light scattered by the particles is detected, characterized in that the particle flow is illuminated and/or observed through a diaphragm aperture with an edge constructed convexly towards its interior, that the maximum intensity of the particles flying through a first optical measuring range is measured and the particles are only taken into account if the intensity on flying through a second measuring range exceeds a given minimum percentage of the maximum intensity measured for these particles.

14. Method according to claim 13, characterized in that as the second measured value determination takes place of the particle intensity after a time period of approximately the average through-flow time of the particle through the first optical measuring range following the determination of the maximum intensity.

15. Method according to claim 13, characterized in that only those particles are detected which, on flowing through the second optical measuring range, give a relative signal intensity of at least 20% of the measured maximum intensity.

* * * * *